United States Patent
Liu

(10) Patent No.: US 10,398,504 B2
(45) Date of Patent: Sep. 3, 2019

(54) ULTRASOUND CATHETER AND MEDICAL SYSTEM USING THE SAME

(71) Applicant: Qisda Corporation, Taoyuan (TW)

(72) Inventor: Jian-Hung Liu, New Taipei (TW)

(73) Assignee: Qisda Corporation, Taoyuan (TW)

(*) Notice: Subject to any disclaimer, the term of this patent is extended or adjusted under 35 U.S.C. 154(b) by 145 days.

(21) Appl. No.: 15/602,050

(22) Filed: May 22, 2017

(65) Prior Publication Data
US 2017/0333123 A1 Nov. 23, 2017

(30) Foreign Application Priority Data
May 23, 2016 (TW) .............................. 105115902 A

(51) Int. Cl.
| | |
|---|---|
| A61B 18/14 | (2006.01) |
| A61B 5/00 | (2006.01) |
| A61F 2/06 | (2013.01) |
| A61M 25/01 | (2006.01) |
| A61B 17/00 | (2006.01) |
| A61B 8/12 | (2006.01) |

(52) U.S. Cl.
CPC ............ A61B 18/1492 (2013.01); A61B 8/12 (2013.01); A61M 25/0105 (2013.01); A61M 2025/0166 (2013.01)

(58) Field of Classification Search
None
See application file for complete search history.

(56) References Cited

U.S. PATENT DOCUMENTS

| | | | |
|---|---|---|---|
| 5,135,001 A * | 8/1992 | Sinofsky | A61B 8/12 600/459 |
| 5,167,637 A | 12/1992 | Okada et al. | |
| 5,618,266 A | 4/1997 | Liprie | |
| 6,921,371 B2 | 7/2005 | Wilson | |
| 7,220,239 B2 | 5/2007 | Wilson et al. | |
| 7,846,101 B2 * | 12/2010 | Eberle | B06B 1/0633 29/25.35 |
| 2004/0068189 A1 | 4/2004 | Wilson et al. | |

FOREIGN PATENT DOCUMENTS

| | | |
|---|---|---|
| CN | 1065999 | 11/1992 |
| CN | 101466314 | 6/2009 |
| JP | 8238244 | 9/1996 |
| JP | 2005211548 | 8/2005 |
| JP | 2006055401 | 3/2006 |

* cited by examiner

*Primary Examiner* — Brian T Gedeon

(57) ABSTRACT

An ultrasound catheter includes a hollow body and a plurality of ultrasound sensing regions. The hollow body is made of a flexible circuit board. The ultrasound sensing regions are disposed on a periphery of the hollow body, wherein each of the ultrasound sensing regions has a plurality of channels, and the channels of each ultrasound sensing region are arranged along an axial direction of the hollow body. A medical system using the ultrasound catheter is also provided.

15 Claims, 5 Drawing Sheets

ULTRASOUND CATHETER AND MEDICAL SYSTEM USING THE SAME

FIELD OF THE INVENTION

The invention relates to an ultrasound catheter and a medical system, and more particularly to an ultrasound catheter and a medical system capable of executing a multi-directional scanning and having a hollow body.

BACKGROUND OF THE INVENTION

An ultrasound catheter enters the blood vessels subcutaneously for a doctor to perform blood vessel scanning, so as to diagnose and treat diseases. A conventional ultrasound catheter includes ultrasound sensing regions disposed on a side of its front end, and thus can only scan a single direction in a single operation. To scan a 360 degree image, a rotating mechanism is needed to be mounted to the rear end of the ultrasound catheter. However, the operation of such arrangement is inconvenient, and the cost is increased. Furthermore, the bodies of conventional ultrasound catheters are all solid tubes, which are unable to be utilized with other treatment equipments, and thus diagnosis and treatment cannot be performed simultaneously.

SUMMARY OF THE INVENTION

It is an object of the present invention to provide an ultrasound catheter and a medical system that can simultaneously scan in multiple directions and have a hollow body to solve the above problems.

According to an embodiment, the ultrasound catheter according to the present invention includes a hollow body and a plurality of ultrasound sensing regions. The hollow body is constructed by flexible circuit board. The flexible circuit board is not only for disposing circuit wires, but also for serving as a constructing base for forming the hollow body. Therefore, the diameter of the hollow body is determined by the size of the flexible circuit board. Ultrasound sensing regions are disposed on a periphery of the hollow body. There are a plurality of channels in each of the ultrasound sensing regions, and each of the channels of the ultrasound sensing regions is arranged along the axial direction of one of the hollow bodies.

According to another embodiment of the present invention, the medical system includes an ultrasound catheter and a treatment equipment. The ultrasound catheter includes a hollow body and a plurality of ultrasound sensing regions. The hollow body is constructed by a flexible circuit board. The ultrasound sensing regions are disposed on a periphery of the hollow body, wherein each one of the ultrasound sensing regions includes a plurality of channels, and each one of the channels of the ultrasound sensing regions is arranged along an axial direction of the hollow body. The spacing between any two adjacent channels must be less than twice of the ultrasound wavelength, so as to form ultrasound images effectively and to reduce the effects of sidelobe and grant lobe. The hollow body includes a front opening and a hole. The treatment equipment enters the hollow body from the hole, and extends from of the hollow body through the front opening.

To sum up, the present invention provides an ultrasound catheter having a hollow body with a plurality of ultrasound sensing regions disposed on its periphery, and each of the ultrasound sensing regions includes a plurality of channels arranged along an axial direction of the hollow body. Since the ultrasound sensing regions enable scanning from different directions, the ultrasound catheter may achieve simultaneous multi-directional scanning without having to install a rotating mechanism. In addition, when a doctor uses an ultrasound catheter to scan for and locate lesions, the doctor may operate the treatment equipment to let it enter the hollow body through the hole of the hollow body and protrude from the hollow body through the front opening of the hollow body. Accordingly, the doctor may perform diagnosis and treatment of lesions simultaneously by utilizing the ultrasound catheter together with the treatment equipment.

Other objectives, features and advantages of the present invention will be further understood from the further technological features disclosed by the embodiments of the present invention wherein there are shown and described preferred embodiments of this invention, simply by way of illustration of modes best suited to carry out the invention.

BRIEF DESCRIPTION OF THE DRAWINGS

The invention will become more readily apparent to those ordinarily skilled in the art after reviewing the following detailed description and accompanying drawings, in which.

DETAILED DESCRIPTION OF PREFERRED EMBODIMENTS

Figure 1:
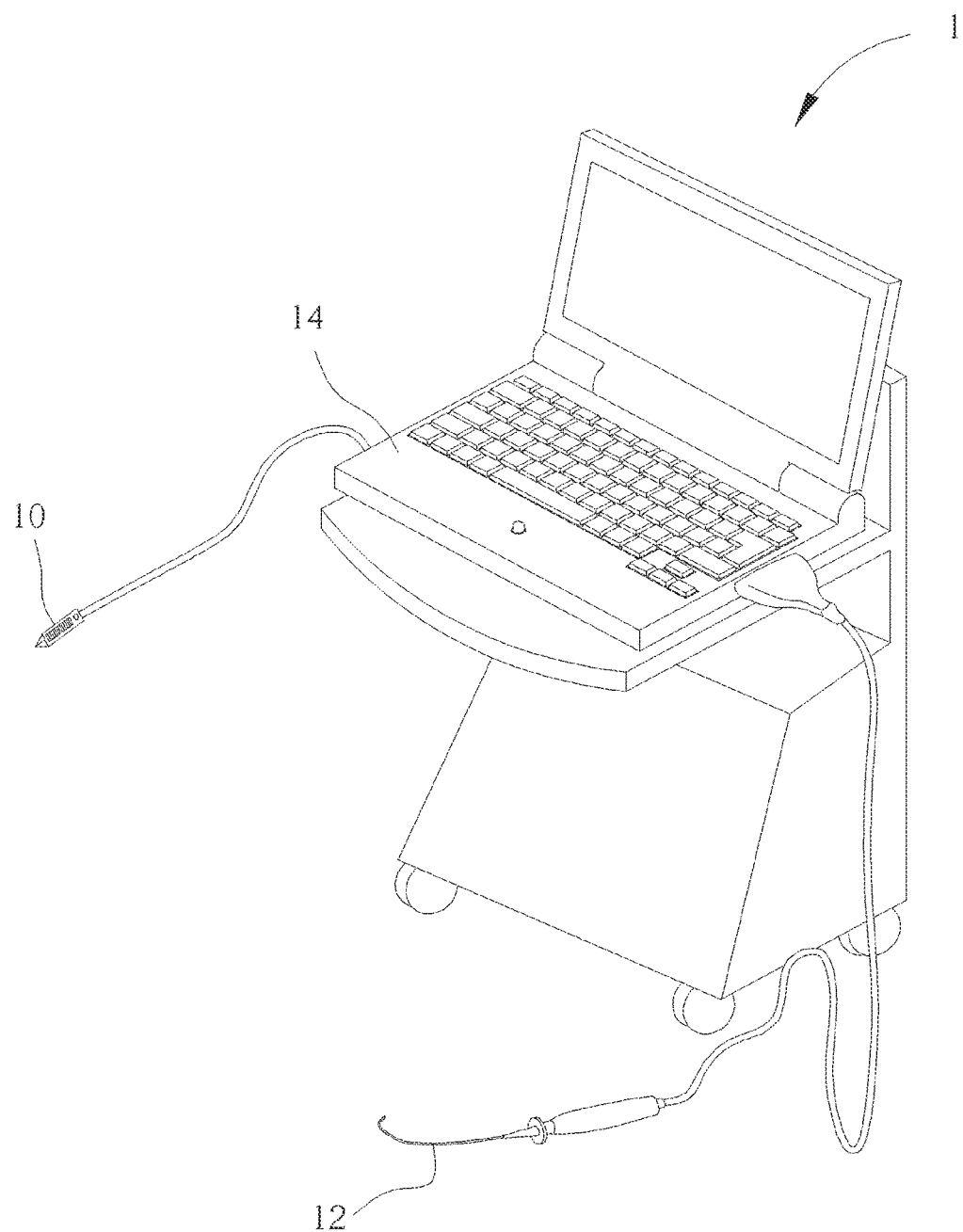
FIG. 1 is a schematic view of a medical system in accordance with an embodiment of the invention.
Figure 2:
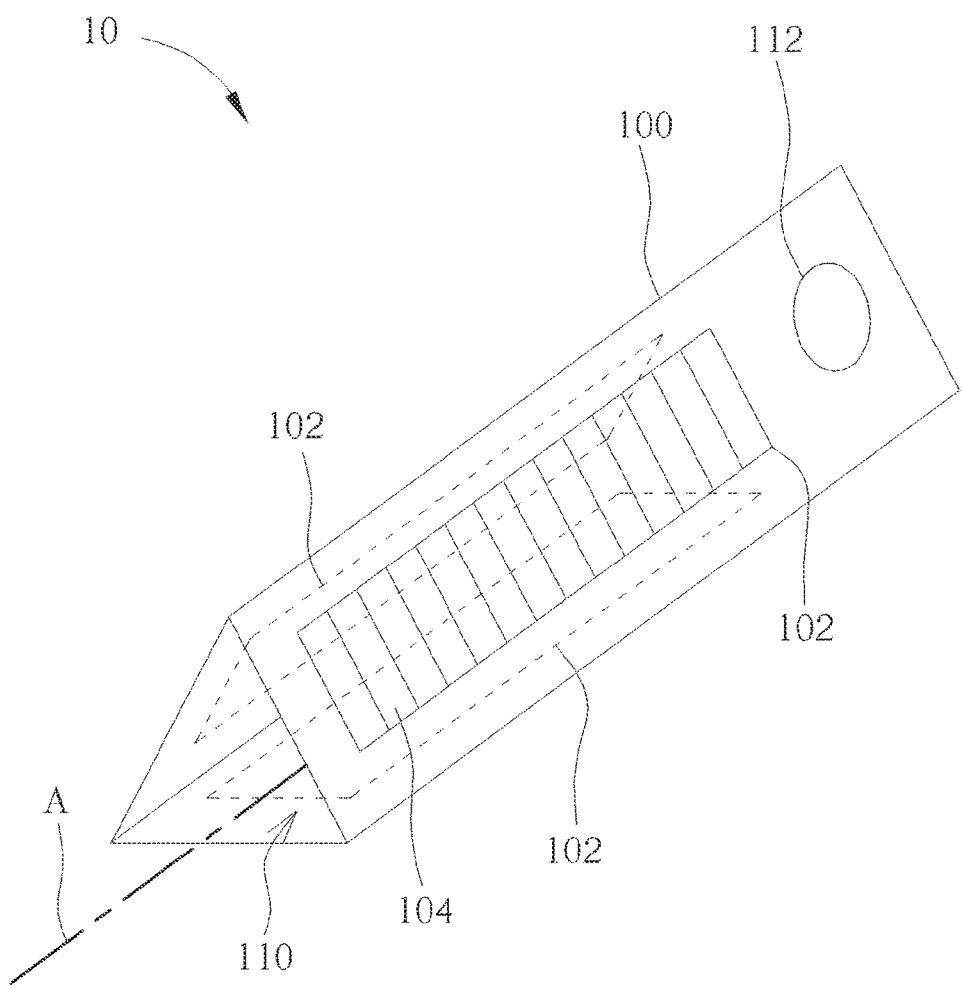
FIG. 2 is a schematic view illustrating the ultrasound catheter of FIG. 1.
Figure 3:
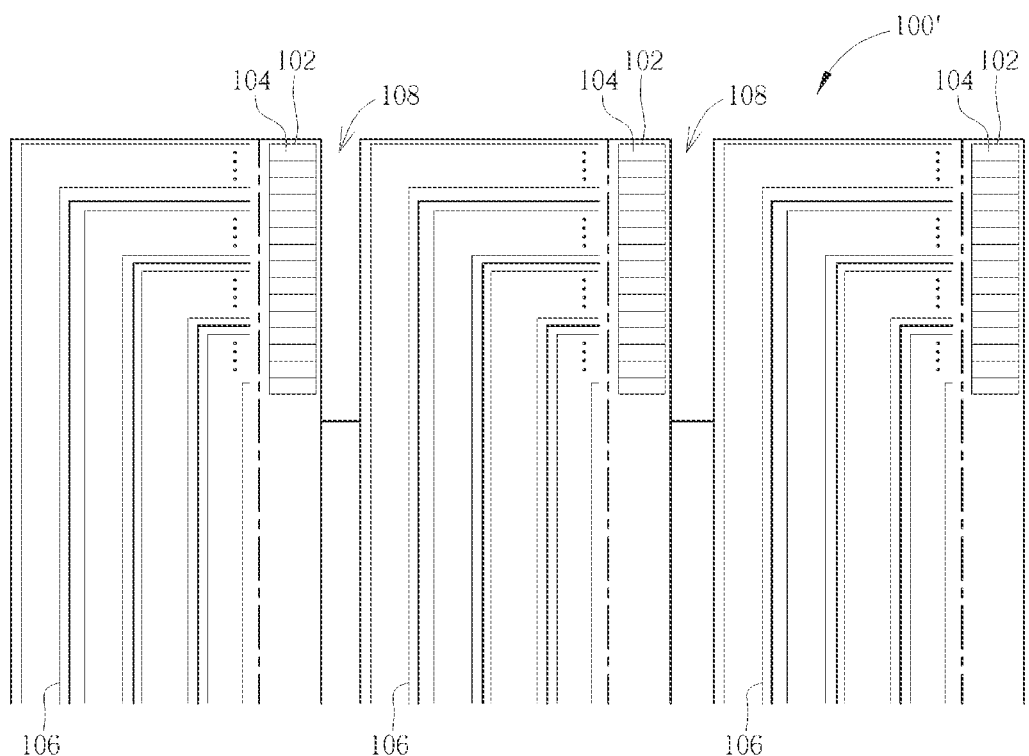
FIG. 3 is a schematic exploded view illustrating the ultrasound catheter of FIG. 2.
Figure 4:
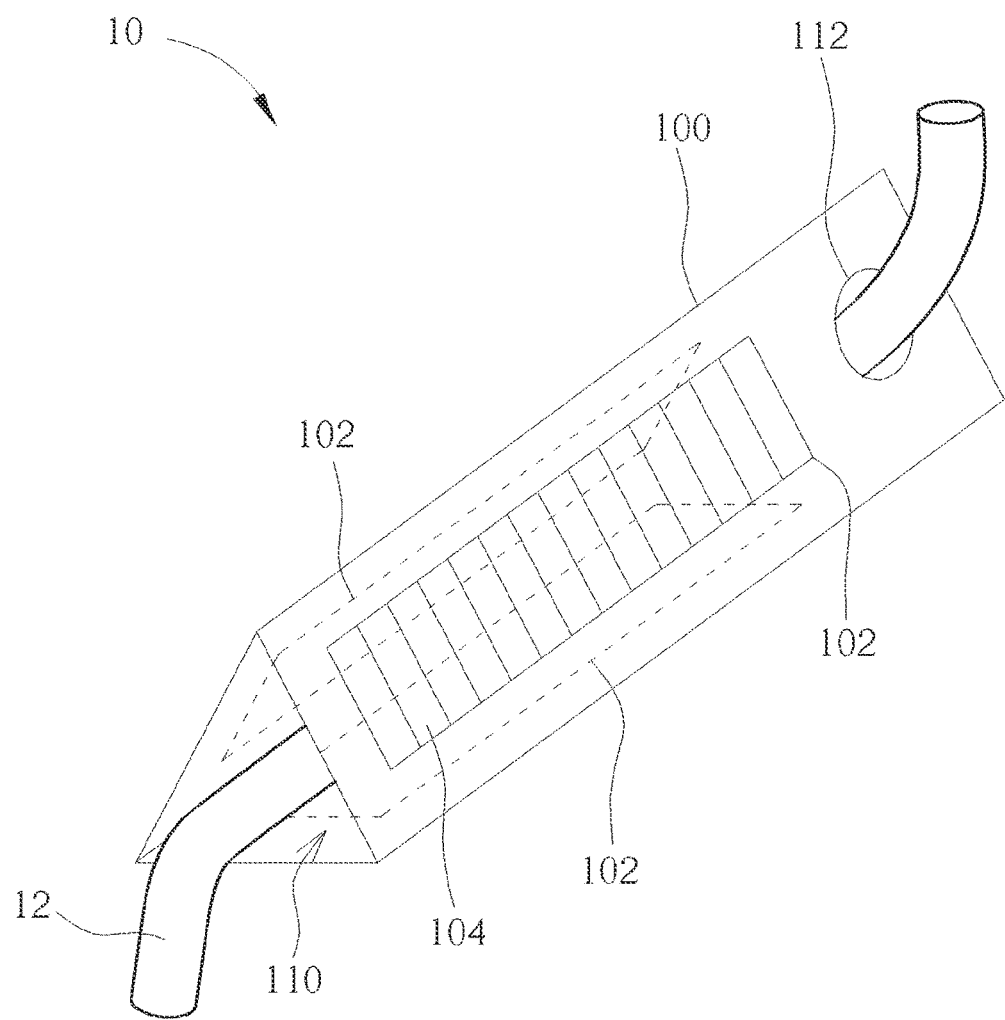
FIG. 4 is a schematic view showing the hollow body of the ultrasound catheter entered by the treatment equipment of FIG. 1.

Please refer to FIG. 1 to FIG. 4. FIG. 1 is a schematic view of a medical system in accordance with an embodiment of the invention, FIG. 2 is a schematic view illustrating the ultrasound catheter 10 of FIG. 1, FIG. 3 is a schematic exploded view illustrating the ultrasound catheter 10 of FIG. 2, and FIG. 4 is a schematic view showing the hollow body 100 of the ultrasound catheter 10 entered by the treatment equipment 12 of FIG. 1.

As shown in FIG. 1, the medical system 1 includes an ultrasound catheter 10, a treatment equipment 12, and a host 14. The host 14 may be a computer or other electric device capable of executing data computing, processing, and illustrating. The ultrasound catheter 10 and the host 14 may communicate with each other via a cable, so that when the ultrasound catheter 10 is scanning an object by ultrasound, the scanned ultrasound image may be shown on the monitor of the host 14. Furthermore, the treatment equipment 12 and the host 14 may also communicate with each other through a cable, so that the doctor may control the treatment equipment 12 through the host 10 to perform related treating operations.

As shown in FIG. 2, the ultrasound catheter 10 includes a hollow body 100 and a plurality of ultrasound sensing regions 102. The ultrasound sensing regions 102 are disposed on the periphery of the hollow body 100. Each of the ultrasound sensing regions 102 includes a plurality of channels 104, and each of the channels 104 of the ultrasound sensing regions 102 is arranged along the axial direction A of the hollow body 100. Therefore, the ultrasound sensing regions 102 are independent of each other, and each of the ultrasound sensing regions 102 may generate an ultrasound image corresponding to its specific angle.

In this embodiment, the hollow body 100 is triangular columnar, and three ultrasound sensing regions 102 are disposed on three side surfaces of the hollow body 100, respectively. Three full ultrasound images generated by the three ultrasound sensing regions 102 may be combined into a circular stereoscopic image in the host 14. It is to be understood that the hollow body 100 may also be a cylinder or other polygonal columnar, and its shape is not limited to triangular columnar. Furthermore, the number of the ultrasound sensing regions 102 may be two or at least three, and is not limited to three.

Each of the ultrasound sensing regions 102 may be made of a piezoelectric material. The piezoelectric material may be lead zirconate titanate (PZT), polyvinylidene (PVDF), $LiNbO_3$, PMNPT or other piezoelectric material. To manufacture the ultrasound catheter 10, a flexible circuit board 100' as shown in FIG. 3 is provided in the present invention, and three ultrasound sensing regions 102 are formed on the flexible circuit board 100', in a manner that the ultrasound sensing regions 102 are electrically connected to circuit wiring 106 of the flexible circuit board 100'. In each of the ultrasound sensing regions 102, each of the channels 104 is connected through the flexible circuit board 100' to the host 14 by an independent signal transmission path (not shown), so that each of the channels 104 may independently perform transmission and reception sequences of different ultrasounds, and thus the ultrasound images may be obtained accordingly. Any two adjacent channels 104 must be spaced apart for a distance less than twice of the wavelength of the ultrasound transmitted by the channels 104, so as to form ultrasound images effectively and to reduce the effects of sidelobe and grant lobe. The number of the channels 104 disposed on each of the ultrasound sensing regions 102 may be 8, 16, 32, 64, 128, 192, 256 or other number, depending on the actual application. Then, the flexible circuit board 100' is bent according to the reserved bending spaces 108, and thus the hollow body 100 as shown in FIG. 2 is formed. More specifically, as shown in FIG. 3, the flexible circuit board 100' is bent according to the fold lines disposed between the channels 104 and the circuit wires 106 of each of the ultrasound sensing regions 102. Accordingly, the side surfaces of the hollow body 100 are formed between the fold lines and the reserved bending spaces 108 allow the side surfaces to form the hollow body 100. The flexible circuit board 100' is not only for disposing the circuit wires 106, but also for serving as a constructing base for forming the hollow body 100. Therefore, the diameter of the hollow body 100 is determined by the size of the flexible circuit board 100'. In practical applications, each of the sensing regions 102 also contains a matching layer, a backing layer, and other necessary components, which are not to be repeated in detail herein.

The doctor may firstly let the ultrasound catheter 10 enter the blood vessel subcutaneously to perform blood vessel scanning so as to diagnose diseases. Since the three ultrasound sensing regions 102 may scan different angles, the ultrasonic catheter 10 of the present invention may achieve simultaneous multi-directional scanning without the need of a rotation mechanism.

In this embodiment, the hollow body 100 includes a front opening 110 and a hole 112, as shown in FIG. 2. When a doctor discovers a lesion by scanning with a ultrasound catheter 10, the doctor may directly operate the treatment equipment 12 to let the treatment equipment 12 enter from the hole 112 on the hollow body 100 into the hollow body 100 and protrude from the front opening 110 of the hollow body 100 into the hollow body 100, as shown in FIG. 4. In this way, the doctor may use the ultrasound catheter 10 with the treatment equipment 12 for diagnosis and treatment of the lesion simultaneously. In practical applications, the treatment equipment 12 may be an electric burner, a balloon stent or other treatment equipment.

Figure 5:
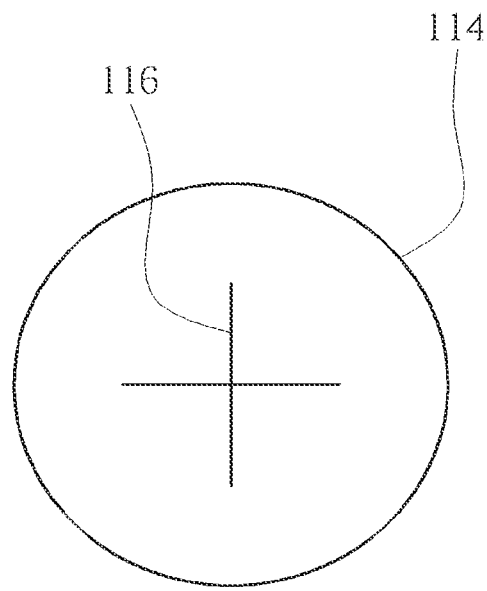
FIG. 5 is a schematic view illustrating an elastic film.

Please refer to FIG. 5. FIG. 5 schematically shows the elastic film 114. In another embodiment, the ultrasound catheter 10 of the present invention may further includes an elastic film 114 as shown in FIG. 5. The elastic film 114 may be a Tegaderm™ transparent film, a polyurethane (PU) film or other film. The present invention may cover the front opening 110 of the hollow body 100 by using the elastic film 114 shown in FIG. 5 in order to prevent blood in the blood vessel from flowing out of the hollow body 100 when the ultrasonic catheter 10 enters the blood vessel for scanning. In addition, the elastic film 114 may have a radial incision 116 so that the treatment equipment 12 may protrude from the front opening 110 of the hollow body 100 through radial incision 116. In practical applications, the radial incision 116 may be of a cross, beige or other shape.

To sum up, according to the present invention, ultrasound sensing regions are disposed on the periphery of the hollow body of an ultrasound catheter, and a plurality of channels of each of the ultrasound sensing regions are arranged along an axial direction of a hollow body. Since a plurality of ultrasound sensing regions may scan at different angles, the ultrasonic device of the present invention may realize simultaneous multi-directional scanning without the need of a rotation mechanism. In addition, when a doctor uses an ultrasound catheter to scan for and locate lesions, the doctor may directly operate the treatment equipment to let it enter from the hole on the hollow body into the hollow body and protrude from the front opening of the hollow body. Accordingly, the doctor may use the ultrasound catheter with the treatment equipment for diagnosis and treatment of the lesions simultaneously.

The foregoing is only a preferred embodiment of the present invention, and all equivalents and modifications of the present invention are intended to be within the scope of the present invention.

What is claimed is:

1. An ultrasound catheter, comprising:
 a hollow body constructed by a flexible circuit board; and
 a plurality of ultrasound sensing regions disposed on a periphery of the hollow body, wherein each of the ultrasound sensing regions is made of a piezoelectric material, each of the ultrasound sensing regions comprises a plurality of channels, and the channels of the ultrasound sensing regions are arranged along an axial direction of the hollow body.

2. The ultrasound catheter according to claim 1, further comprising an elastic film covering a front opening of the hollow body.

3. The ultrasound catheter according to claim 2, wherein the elastic film comprises a radial incision.

4. The ultrasound catheter according to claim 1, wherein the hollow body is triangular columnar, the number of the ultrasound sensing regions is three, and the three ultrasound sensing regions are disposed on three side surfaces of the hollow body, respectively.

5. The ultrasound catheter according to claim 1, wherein to form the hollow body, the flexible circuit board is bent according to a plurality of fold lines respectively disposed between the channels and circuit wires disposed on the flexible circuit board within each of the ultrasound sensing regions.

6. The ultrasound catheter according to claim 1, wherein each of the channels is connected through the flexible circuit board to a host independently, so that the channels are capable of independently performing transmission and reception sequences of different ultrasounds.

7. The ultrasound catheter according to claim 1, wherein any two of the channels that are adjacent to each other are spaced apart for a distance less than twice of a wavelength of an ultrasound transmitted by the channels.

8. A medical system, comprising:
an ultrasound catheter, comprising a hollow body, an elastic film and a plurality of ultrasound sensing regions, wherein the hollow body is constructed by a flexible circuit board, the ultrasound sensing regions are disposed on a periphery of the hollow body, each of the ultrasound sensing regions comprises a plurality of channels, the plurality of channels of each of the ultrasound sensing regions are arranged along an axial direction of the hollow body, the hollow body comprises a front opening and a hole, and the elastic film covers the front opening of the hollow body; and
a treatment equipment, wherein the treatment equipment enters the hollow body through the hole and protrudes from the hollow body through the front opening.

9. The medical system according to claim 8, wherein each of the ultrasound sensing regions is made of a piezoelectric material.

10. The medical system according to claim 8, wherein the elastic film comprises a radial incision, and the treatment equipment passes through the radial incision and extrudes from the hollow body through the front opening.

11. The medical system according to claim 8, wherein the hollow body is triangular columnar, the number of the ultrasound sensing regions is three, and the three ultrasound sensing regions are disposed on three side surfaces of the hollow body, respectively.

12. The medical system according to claim 8, wherein the treatment equipment is an electric burner or a balloon stent.

13. The medical system according to claim 8, wherein to form the hollow body, the flexible circuit board is bent according to a plurality of fold lines respectively disposed between the channels and the circuit wires disposed on the flexible circuit board within each of the ultrasound sensing regions.

14. The medical system according to claim 8, wherein each of the channels is connected through the flexible circuit board to a host independently, so that the channels are capable of independently performing transmission and reception sequences of different ultrasounds.

15. The medical system according to claim 8, wherein any two of the channels that are adjacent to each other are spaced apart for a distance less than twice of a wavelength of an ultrasound transmitted by the channels.

* * * * *